United States Patent [19]

Webb et al.

[11] Patent Number: 5,239,102

[45] Date of Patent: Aug. 24, 1993

[54] METHOD FOR MAKING ORGANOHALOSILANES

[75] Inventors: Steven W. Webb, Clifton Park; Alan Ritzer, Sand Lake; John D. Neely, Clifton Park, all of N.Y.

[73] Assignee: General Electric Company, Schenectady, N.Y.

[21] Appl. No.: 867,656

[22] Filed: Apr. 13, 1992

[51] Int. Cl.$^5$ ............................................... C07F 7/16
[52] U.S. Cl. .................................................. 556/472
[58] Field of Search ........................................ 556/472

[56] References Cited

U.S. PATENT DOCUMENTS

| | | | |
|---|---|---|---|
| 2,803,521 | 8/1957 | Nitzsche et al. | 556/472 X |
| 4,281,149 | 7/1981 | Shade | 556/472 |
| 4,328,353 | 5/1982 | Shah | 556/472 |
| 4,450,282 | 5/1984 | Ritzer et al. | 556/472 |

*Primary Examiner*—Paul F. Shaver
*Attorney, Agent, or Firm*—William A. Teoli; William H. Pittman

[57] ABSTRACT

A method for making organohalosilanes is provided utilizing a spent contact mass generated during the production of organohalosilanes by the direct method which has been thermally treated to render it non-reactive in air.

7 Claims, No Drawings

METHOD FOR MAKING ORGANOHALOSILANES

CROSS REFERENCE TO RELATED APPLICATION

Reference is made to copending application Ser. No. 07/867,657, which is filed concurrently herewith.

BACKGROUND OF THE INVENTION

The present invention relates to a method for making organohalosilanes by the direct reaction of an organic halide such as methylchloride and powdered silicon in the presence of a copper catalyst. More particularly, the present invention relates to the employment of thermally treated spent direct method contact mass as a make-up catalyst and silicon source for the direct production of organohalosilanes.

Prior to the present invention, organohalosilanes were generally made by the direct reaction of an organic halide and powdered silicon in the presence of a copper catalyst as shown by Rochow U.S. Pat. No. 2,380,995. It was found that as the reaction proceeded the silicon powder became spent which adversely affected yield and selectivity.

Rossmy, U.S. Pat. No. 3,069,452 teaches that improved yields and selectivity of organohalosilanes can be obtained if the copper catalyst used in the Rochow synthesis is replaced with a brittle easily grindable silicon-copper alloy having from 50% to 99% by weight copper and preferably about 12.8% silicon. The silicon copper alloy is then finely ground and mixed with silicon powder and the resulting mixture is sintered in an inert atmosphere prior to reaction with organic halide.

In Shade, U.S. Pat. No. 4,281,149, particles of silicon and copper of less than 40 microns average diameter which were generated during the Rochow process are removed from the reactor, abraded and then returned to the reactor. In Shah et al, U.S. Pat. No. 4,307,242, a portion of direct process contact mass is analyzed for particle size distribution, classified and segregated into a silicon rich fraction which can be returned to the reactor, and a silicon poor fraction which can be removed from the reactor.

In copending application Ser. No. 07/867,657, there is described a method for passivating or stabilizing spent silicon contact mass generated during the direct method for making organohalosilanes by the reaction between silicon powder and an organic halide such as methylchloride. Spent silicon contact mass can have an average particle size in the range of 0.1 to 200 microns. It is difficult to manage because it is pyrophoric in air and cannot be readily moved to an appropriate waste disposal site or be reused. Treatment of spent silicon contact mass by heating it at a temperature in the range of about 900° C. to about 1400° C. under an inert atmosphere has been found to render the spent contact mass substantially unreactive in air and more easily handled. The treating procedure of copending application Ser. No. 07/867,657 provides a significant advance over prior art, methods such as shown by Hosokawa, U.S. Pat. No. 4,724,122, requiring the combining of the spent silicon contact mass with water and granulating the mixture followed by coating the resulting granules with an inert organic powder. Offenlegungschrift DE 313 1732A1 and U.S. Pat. No. 4,758,352 to Feldner et al. also describe procedures for reprocessing residues produced during organohalosilane synthesis. Unlike copending application Ser. No. 07/867,657, the residues from DE 313 1732A1 and U.S. Pat. No. 4,758,352 are derived from sludge vessels which consist of siliceous solids and liquids such as polysilanes. It is desirable therefore to provide additional procedures for making organohalosilane from spent powders while minimizing waste.

SUMMARY OF THE INVENTION

The present invention is based on the discovery that spent direct method contact mass which has been thermally treated by being heated in an inert atmosphere at temperatures sufficient to render it substantially nonreactive in air, can be recycled and used with organic halide either directly or in combination with silicon powder and direct method catalyst, to generate additional organohalosilanes.

STATEMENT OF THE INVENTION

There is provided by the present invention a process for making organohalosilanes by the direct method, comprising effecting reaction between an organic halide and a mixture comprising silicon powder, an effective amount of direct method catalyst, and spent direct method contact mass which has been thermally treated in an inert atmosphere under conditions sufficient to render it substantially nonreactive in air at temperatures up to 350° C., where the treated spent direct method contact mass is used directly or in combination with silicon powder and direct method catalyst in an amount sufficient to maintain during organohalosilane production, from about 0.1 to about 10% by weight of copper relative to silicon.

The spent contact mass treated in accordance with the practice of the method of the present invention can have a particle size in the range of from 0.1 to 200 microns. Treatment of the spent contact mass can be effected at temperatures in the range of about 900° C. to about 1400° C. under an inert atmosphere. The spent silicon contact mass which can be treated in accordance with the present invention and further employed in generating organohalosilanes can have a surface area of up to about 25 m$^2$/g. Spent silicon contact mass which can be treated and used in the generation of organohalosilanes in accordance with the invention include materials shown by Marko et al, U.S. Pat. No. 5,000,934, Hosokawa, U.S. Pat. No. 4,724,122 and Ritzer et al, U.S. Pat. No. 4,892,694, which are incorporated herein by reference.

In the practice of the preferred form of the invention, spent silicon contact mass is treated after it has been collected from an organohalosilane reactor, and can be recycled with powdered silicon and direct method catalyst which hereinafter means copper catalyst, or a mixture of copper catalyst and one or more promoters such as zinc. Suitable copper catalysts include carboxylic acid salts of copper, such as copper formate, partially oxidized copper as well as copper salts such as cupric chloride, cuprous chloride, and copper metal particulate. Promoters which can be employed with copper catalyst are zinc metal, zinc dust or a zinc compound such as zinc oxide. Other promoters include tin metal, and tin compounds, such as tin oxide and tin halides such as tin tetrachloride.

If desired the spent silicon contact mass can be treated and stored prior to being recycled in the organohalosilane reactor, for example, the spent silicon contact mass can be collected in a hopper under an inert gas atmosphere such as a nitrogen atmosphere. Alternatively, it can be conveyed directly to a thermal treatment zone shortly after it is generated under direct process conditions. Suitable means for heating the spent silicon contact mass to an appropriate treatment temperature as previously defined are, for example, a calcining furnace or a rotary kiln. Venting of reaction gases, such as surface chlorosilanes evolved during treatment can be facilitated by the employment of an inert gas, such as nitrogen or a noble gas such as argon which can also serve to maintain a substantially inert atmosphere. Although a temperature of between about 900° C. to 1400° C. can be used to treat these spent silicon spent contact mass, a temperature of about 1000 C to 1200° C. is preferred and a temperature of about 1050° C. to 1100° C. is particularly preferred. Duration of treatment can vary in the range of from about 0.05 to 1 hour depending upon the temperature employed and the specific characteristics of the spent contact mass. The stored powder after it has been treated can be recycled to an organohalosilane reactor. If desired the treated spent contact mass can be introduced into the reactor with makeup powdered silicon along with additional proper catalyst and metallic promoters in a batchwise or continuous manner.

In order that those skilled in the art will be better able to practice the present invention, the following examples are given by way of illustration and not by way of limitation. All parts are by weight unless otherwise indicated.

EXAMPLE 1

Spent reactor contact mass which was found to be pyrophoric in air was obtained from the reaction of metallic silicon powder and methylchloride under direct method conditions. The contact mass was thermally treated at 1100° C. for 3 minutes in nitrogen. The treated contact mass was then placed in a 2" stirred bed reactor exposed to flowing methylchloride at 300° C. The same procedure was repeated except that untreated spent contact mass was used. The activity of the treated and untreated contact mass was compared. Activity was expressed in milligrams of recovered condensable silane product per gram of initial powder per hour. Silane monomer selectivity is expressed as the weight ratio of methyltrichlorosilane, "T", to dimethyldichlorosilane, "D", or, "T/D"; silicon yield is expressed as grams of silicon utilized per gram of initial silicon. The following results were obtained:

TABLE 1

| Treated Contact Mass | | | Untreated Contact Mass | | |
|---|---|---|---|---|---|
| Yield (g/g) | Rate (mg/g/hr) | T/D | Yield (g/g) | Rate (mg/g/hr) | T/D |
| 0.02 | 104 | 0.094 | 0.017 | 85 | 0.117 |
| 0.20 | 483 | 0.066 | 0.14 | 274 | 0.048 |
| 0.31 | 420 | 0.047 | 0.20 | 275 | 0.050 |
| 0.41 | 321 | 0.048 | 0.28 | 305 | 0.055 |
| 0.44 | 161 | 0.139 | 0.38 | 50 | 1.78 |
| 0.45 | 11 | 1.15 | 0.40 | 38 | 2.14 |
| 0.46 | 12 | 2.04 | 0.40 | 7 | 2.78 |

The above results show that the contact mass treated in accordance with the practice of the invention provides improved yield, rate and selectivity performance as compared to untreated spent reactor contact mass.

EXAMPLE 2

A mixture of one part of treated spent reactor contact mass of example 1 and two parts of chemical grade silicon powder having an average particle size of 30 microns was employed in the stirred bed reactor of example 1 and exposed to methylchloride at 300° C. The same procedure was repeated except that untreated spent contact mass without additional zinc was substituted for the contact mass treated in accordance with the practice of the invention. Activity, silane monomer selectivity and silicon yield were then determined. The results are shown in Table 2 below.

TABLE 2

| Treated Contact Mass | | | Untreated Contact Mass | | |
|---|---|---|---|---|---|
| Yield (g/g) | Rate (mg/g/hr) | T/D | Yield (g/g) | Rate (mg/g/hr) | T/D |
| 0.01 | 57 | 0.665 | 0.03 | 98 | 0.251 |
| 0.19 | 212 | 0.231 | 0.13 | 195 | 0.200 |
| 0.28 | 71 | 0.252 | 0.16 | 49 | 0.704 |
| 0.35 | 36 | 0.241 | 0.17 | 31 | 0.927 |
| 0.36 | 62 | 0.246 | 0.17 | 7 | 1.35 |
| 0.47 | 88 | 1.258 | 0.18 | 17 | 0.998 |
| 0.60 | 30 | 2.591 | 0.185 | 21 | 0.804 |

The above results show that spent reactor contact mass treated in accordance with the invention and further blended with chemical grade silicon powder can provide enhanced silicon yield, activity and selectivity as compared to untreated spent contact mass.

EXAMPLE 3

There was added to the stirred bed reactor of example 1, a first mixture of about 24% by weight of treated contact mass of example 1, about 71.5% by weight of powdered silicon, and about 4.1% by weight of direct method catalyst having about 2.3% by weight of elemental copper. The mixture was exposed to methylchloride at 300° C. The same procedure was repeated except a mixture of the silicon powder and sufficient direct method catalyst substantially equivalent to the direct method catalyst of the first mixture was used. The second mixture was exposed to methylchloride at 300° C. in the stirred bed reactor. Activity and selectivity of the mixtures were compared. The following results were obtained where "TCM" is treated contact mass, "SP" is silicon powder and "DMC" is direct method catalyst:

TABLE 3

| TCM + SP + DMC | | | SP + DMC | | |
|---|---|---|---|---|---|
| Yield (g/g) | Rate (mg/g/hr) | T/D | Yield (g/g) | Rate (mg/g/hr) | T/D |
| 0.133 | 265 | 0.208 | 0.143 | 322 | 0.247 |
| 0.248 | 174 | 0.223 | 0.222 | 289 | 0.169 |
| 0.31 | 140 | 0.210 | 0.300 | 356 | 0.124 |
| 0.33 | 126 | 0.190 | 0.382 | 299 | 0.120 |
| | | | 0.518 | 260 | 0.311 |

The above results show that treated contact mass is useful as a source of silicon and direct method catalyst when used in the direct method for making organohalosilanes.

What is claimed is:

1. A process for making organohalosilanes by the direct method, comprising effecting reaction between an organic halide and a mixture comprising silicon powder, an effective amount of direct method catalyst, and spent direct method contact mass having a particle size in the range of 0.1 to 200 microns which has been thermally treated in an inert atmosphere under conditions sufficient to render it substantially nonreactive in air at temperatures up to 350° C., where the treated spent direct method contact mass is used directly or in combination with silicon powder and direct method catalyst in an amount sufficient to maintain during organohalosilane production, from about 0.1 to about 10% by weight of copper relative to silicon.

2. A batch process for making organohalosilanes in accordance with claim 1.

3. The continuous process in a fluid bed reactor for making organohalosilanes in accordance with claim 1.

4. A process for making organohalosilanes in accordance with claim 1, using a stirred bed reactor.

5. A process in accordance with claim 1, using a fixed bed reactor.

6. A process in accordance with claim 1, utilizing a copper-zinc-tin catalyst.

7. A process in accordance with claim 1, where the copper catalyst is partially oxidized copper.

* * * * *